United States Patent
Burbank et al.

(10) Patent No.: US 6,193,684 B1
(45) Date of Patent: *Feb. 27, 2001

(54) DEVICE FOR PERCUTANEOUS PERITONEAL DIALYSIS

(75) Inventors: Jeffrey H. Burbank, Boxford; James M. Brugger, Newburyport, both of MA (US)

(73) Assignee: Vasca, Inc., Tewksbury, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/896,791

(22) Filed: Jul. 18, 1997

Related U.S. Application Data

(60) Provisional application No. 60/036,124, filed on Jan. 21, 1997.

(51) Int. Cl.[7] ............................. A61M 1/00; A61M 11/00
(52) U.S. Cl. ............................. 604/29; 604/93.01
(58) Field of Search ......................... 604/891.1, 8, 9, 604/27, 28–30, 32, 33, 34, 49, 51, 93, 264, 272, 410, 29, 506, 513; 251/7

(56) References Cited

U.S. PATENT DOCUMENTS

| | | | |
|---|---|---|---|
| 4,190,047 | * | 2/1980 | Jacobsen et al. ............. 604/29 |
| 4,239,041 | * | 12/1980 | Popovich et al. .............. 604/28 |
| 4,493,696 | * | 1/1985 | Uldall ............................. 604/43 |
| 4,832,054 | * | 5/1989 | Bark ................................. 604/9 |
| 5,041,098 | * | 8/1991 | Loiterman et al. ............ 604/93 |
| 5,336,165 | * | 8/1994 | Twardowski .................... 604/5 |
| 5,782,796 | * | 7/1998 | Din et al. ....................... 604/29 |

* cited by examiner

Primary Examiner—Sharon Kennedy
(74) Attorney, Agent, or Firm—Townsend and Townsend and Crew LLP

(57) ABSTRACT

The present invention is generally directed to delivering liquid compositions to an interior site in the body. More particularly, the present invention provides devices, systems, and methods for facilitating percutaneous access to an implantable port for performing peritoneal dialysis in a sterile condition. In one aspect, the present invention provides an apparatus for use in peritoneal dialysis comprising a first container and a second container, wherein at least one of the containers is filled with unused dialysis fluid. The first and second containers are fluidly coupled by a first tube and a second tube to a junction, respectively. A single common tube fluidly coupled to the junction provides a fluid pathway to a percutaneous access member connected to the end of the single common tube. The access member has a minimum bore diameter of 1.16 mm capable of providing high volumetric flow rates.

36 Claims, 8 Drawing Sheets

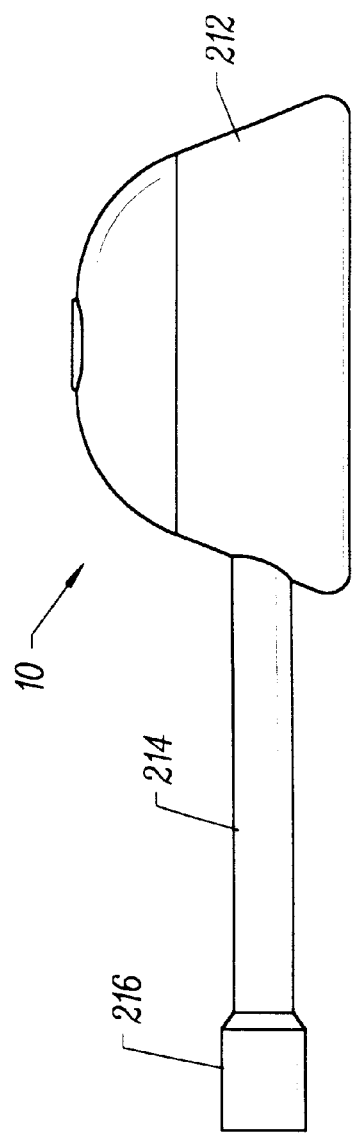
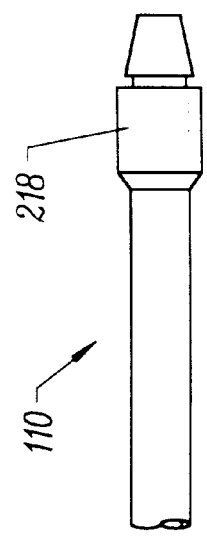
FIG. 4

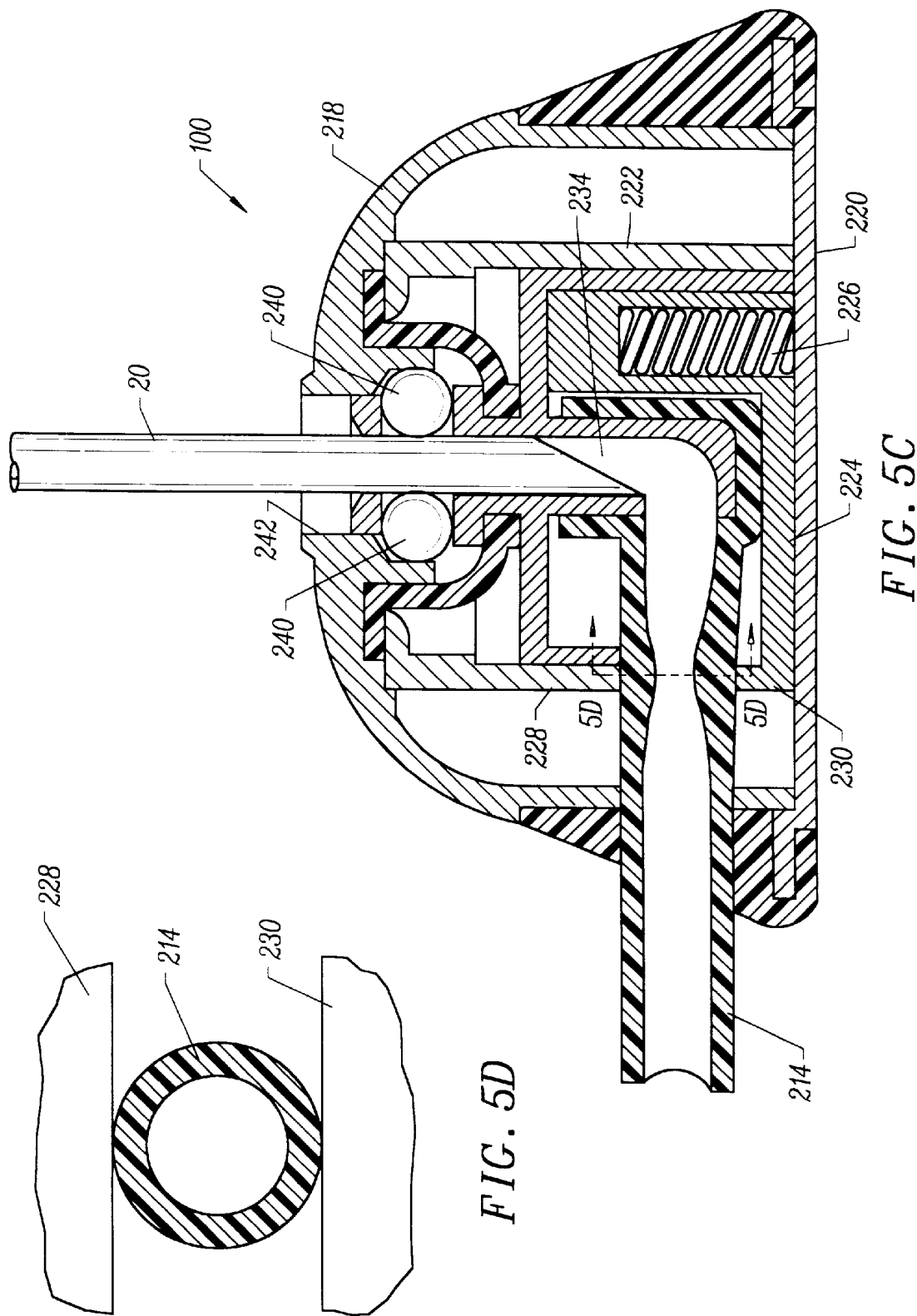

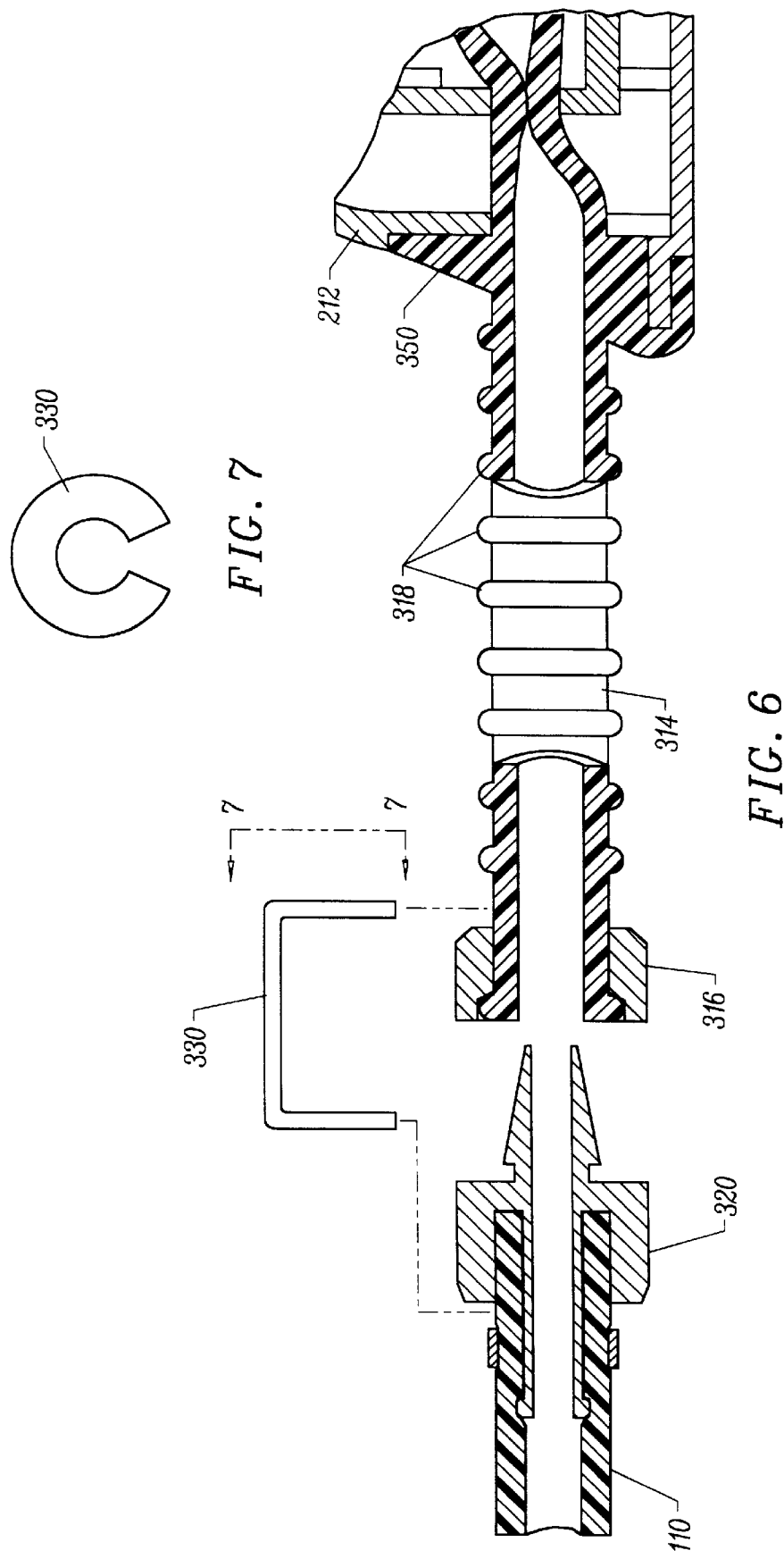

DEVICE FOR PERCUTANEOUS PERITONEAL DIALYSIS

CROSS-REFERENCE TO RELATED APPLICATION

The present invention is a continuation-in-part of provisional Application Ser. No. 60/036,124, filed on Jan. 21, 1997. The present application is also related to U.S. Pat. No. 5,997,524 and 5,989,239, each of which were filed on the same day as the present application. The full disclosures of each of these patents are incorporated herein by reference.

BACKGROUND OF THE INVENTION

1. Field of the Invention

The present invention is generally directed to delivering liquid compositions to an interior site in the body. More particularly, this invention relates to delivering and draining compositions to and from a human patient at high flow rates to perform peritoneal dialysis under sterile conditions.

Patients afflicted with end stage renal disease where kidney transplantation is unavailable may be treated by hemodialysis or peritoneal dialysis to remove toxic products from the patient's blood. Both techniques operate by the principles of diffusion across semipermeable membranes. In the case of peritoneal dialysis, the membrane that is used is the patient's peritoneal membrane. In order to perform dialysis, a dialyzing solution or dialysate is drained into the peritoneal cavity and remains in the cavity for a dwell period of usually four to six hours. The dialyzing solution typically comprises an electrolyte component to reduce loss of electrolytes and a sugar component which acts as an anosmotic ingredient, removing water from the patient along with normal metabolic products such as urea, uric acid and creatinine. At the end of the dwell period, spent dialyzing solution is drained from the cavity back to the bag and the cavity refilled with fresh solution.

One serious drawback to peritoneal dialysis, which has limited its use, is that the peritoneal cavity is particularly subject to infection. Conventional peritoneal dialysis systems usually employ catheters which are implanted transcutaneously through the patient's abdomen. This exposure naturally increases the risk of contamination through the exposed, exterior end of the catheter. The tubing sets used to infuse solution into the peritoneum may also be a source of contamination. While the use of subcutaneously implanted septum-type ports has been suggested (such ports would be accessed with needles which reduces the chance of infection), the access with small bore non-coring needles places a flow restriction in the system which reduces the flow rate below the rate achieved by transcutaneous catheters. Such small bore access needles with relatively low flow rates prolong the exchange time and create additional patient discomfort.

2. Description of the Background Art

Conventional peritoneal dialysis tubing sets and components are described in U.S. Pat. Nos. 4,306,976; 4,396,382; 5,250,041; 5,334,139; 5,338,293; and 5,423,768. U.S. Pat. No. 4,184,497 describes an implantable catheter having an enlarged hollow portion which can be punctured to receive a sterile access needle. U.S. Pat. No. 4,496,349 describes a septum-type transcutaneous access port.

SUMMARY OF THE INVENTION

The present invention is directed at reducing the time needed to exchange dialysis fluid and limiting the risk of infection to the peritoneal cavity. More particularly, the present invention allows the use of large bore, percutaneous access members to deliver and drain fluid from the peritoneal cavity at high volumetric flow rates under sterile conditions, typically above 100 ml/min, preferably 200 ml/min, or higher.

In a first aspect, the present invention provides an apparatus for use in peritoneal dialysis in combination with a first container and a second container. The apparatus comprises a junction connected to a first and a second tube which are connected and/or connectable to the first and second containers, respectively. At least one of the containers is filled with unused dialysis fluid. A single common tube, fluidly coupled to the junction, fluidly connects the first and second tubes to a percutaneous access member having a bore diameter of at least 1.16 mm. Preferably, the percutaneous access member is straight and has a length in the range from about 15 mm to 40 mm, preferably from about 18 mm to 26 mm. The access member usually has a relatively large bore, typically having a lumenal diameter in the range from about 1 mm to 5 mm, preferably from about 1.5 mm to 2.1 mm. In specific embodiments of the apparatus of the present invention, the percutaneous access member comprises a large bore needle, such as a fistula-type needle. The large bore access members are advantageous in minimizing flow resistance and allowing for higher volumetric flow rates to and from the patient.

In another aspect, the present invention provides a system for performing peritoneal dialysis comprising a peritoneal dialysis tubing set having an access member and a mechanical port. The port has an aperture for receiving the access member of the tubing set and a flexible conduit in the port disposed to establish fluid flow with the access member inserted through the first passage. A linkage assembly in the port opens the flexible conduit when the access member is present in the passage and closes the flexible conduit when the access member is absent from the passage. The system may further comprise a peritoneal dialysis catheter fluidly coupled to the flexible conduit. The port allows for the advantageous use of large bore access members which would otherwise core and damage conventional septum-type ports.

In a further aspect, the present invention provides a method for performing peritoneal dialysis comprising the step of accessing a mechanical valve port coupled to a patient with an access member. Unused dialysis solution is introduced to the patient's peritoneal cavity through the access member and the mechanical port. After the dialysis solution has been in the patient for a specified dwell period, the dialysis solution is withdrawn from the patient's peritoneal cavity through the port and the access member. Preferably, the access member has a minimum bore diameter of 1.16 mm.

These and other embodiments of the present invention, as well as its advantages and features, are described in more detail in conjunction with the text below and attached figures.

BRIEF DESCRIPTION OF THE DRAWINGS

FIG. 4 illustrates a implantable mechanical port of the present invention, wherein the flexible conduit is adapted for connection to a separate catheter.

FIG. 5C is a side, cross-sectional view of the port of FIG. 4 as shown with the internal valve structure opened in response to the insertion of an access needle.

FIG. 5D is a partial cross-sectional view taken along line 5D—5D of FIG. 5C.

FIG. 6 is a partial, cross-sectional view of a specific flexible conduit having a distal connector for interconnection to the proximal end of an implantable catheter.

FIG. 7 is an end view taken along line 7—7 of FIG. 6.

DETAILED DESCRIPTION OF THE SPECIFIC EMBODIMENTS

The present invention is generally directed to delivering liquid compositions to an interior site in the body. More particularly, the present invention provides devices, systems, and methods for facilitating percutaneous access to an implantable mechanical port for performing peritoneal dialysis in a sterile condition. Typical forms of peritoneal dialysis require the delivery and subsequent draining of a dialysis solution or dialysate from the peritoneal cavity. The dialysate typically comprises a solution which will promote diffusion or osmosis across a patient's peritoneal membrane so as to remove toxic by-products from the patient's blood. In particular forms of peritoneal dialysis such as Continuous Ambulatory Peritoneal Dialysis (CAPD), the dialysate, after initial delivery into the peritoneal cavity, remains in the cavity for a dwell period of usually 4 to 6 hours. During this time, the dialysate removes normal metabolic products such as urea, uric acid, and creatinine from the patient's body. At the conclusion of the dwell period, the used dialysate or dialysis solution is removed from the peritoneal cavity and typically replaced by a new supply of unused dialysate.

Advantageously, the ports and access systems of the present invention can achieve inflow and outflow rates as high as those achieved with transcutaneous catheters, i.e. usually about 100 ml/min, often at or above 200 ml/min. These rates are limited by the characteristics of the peritoneal cavity itself. Prior art implanted septum ports added significant flow resistance to the access systems, usually reducing inflow and/or outflow well below 200 ml/min.

Figure 1:
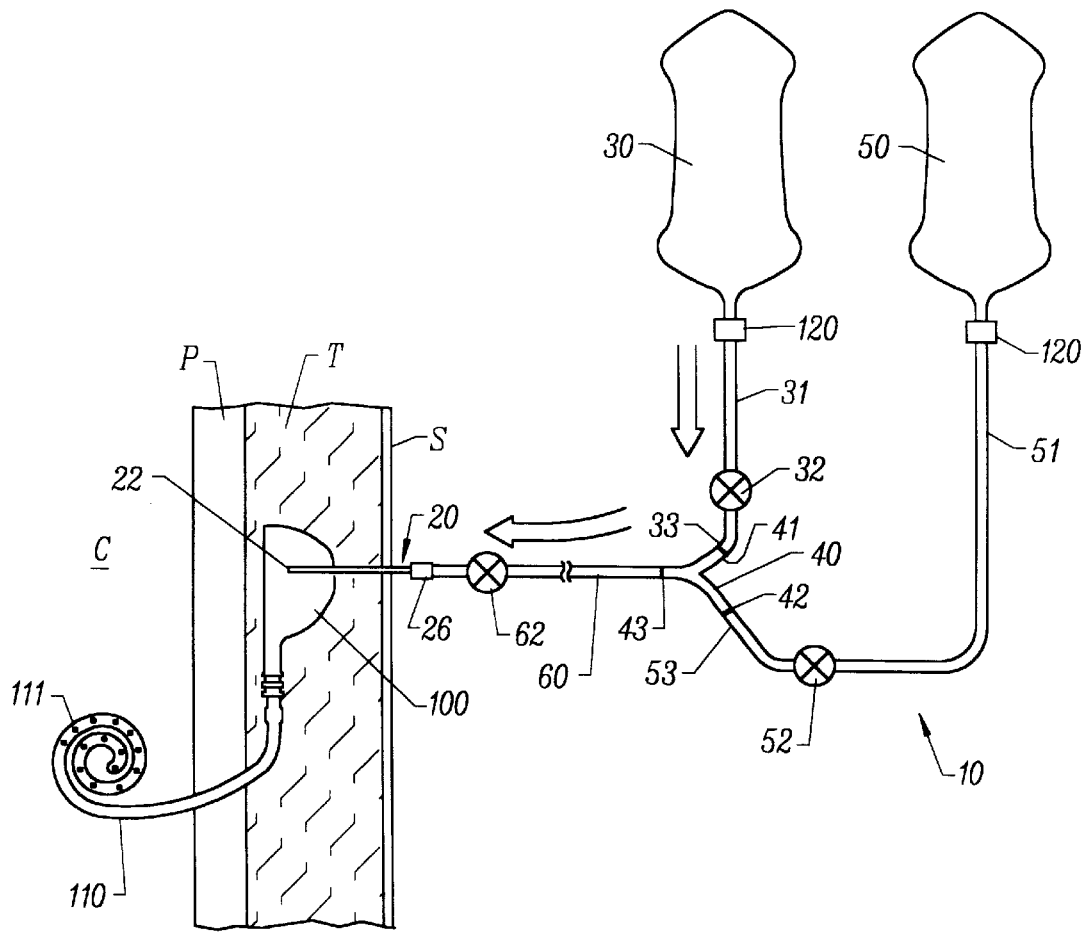
FIG. 1 is a schematic illustration of one embodiment of the system of the present invention.

As shown in FIG. 1, a peritoneal dialysis tubing set 10 having a percutaneous access member 20 is used to deliver and drain the dialysate from the patient's peritoneal cavity. In preferred embodiments, the peritoneal dialysis tubing set 10 comprises at least a first container 30, a first tube 31 and a second tube 51. Optionally, a second container 50 may also be provided in the tubing set 10. The first tube 31 is connected or connectable to the first container 30 while the second tube is connected or connectable to the second container 50, usually through a junction 40, which is typically a Y-type connector. As used herein after, the term Y-connector will also comprise other three-way connectors, such as T-connectors. A fluid flow controller 32 on tube 31 and a controller 52 on tube 51 regulate dialysate flow in the tubes. These fluid flow controllers 32 and 52 may completely stop fluid flow to or from their respective containers, or the fluid flow controllers may simply increase or decrease the flow rates.

Percutaneous access member 20, typically a needle having a sharpened distal tip 22 extends from single common tube 60 which is fluidly coupled to junction 40. The access member will leave a large bore, as defined below. Access members useful in the present invention may conveniently comprise large bore coring needles, such as conventional fistula needles. By "coring needles," it is meant that the distal tip of the needle will be sharpened and will be open in a forwardly direction so that the needle is capable of cutting tissue (and "coring" septums when encountered) as it is advanced therethrough in a forwardly direction. The present invention may also utilize needles having a non-coring design, such as Huber needles which have a side-facing distal opening. The needles will have a bore size of at least 1.16 mm (16 G), usually at least 1.33 mm (15 G), more usually at least 1.55 mm (14 G), still more usually at least 1.73 mm (13 G), and sometimes as large as 2.08 mm (12 G), or larger. The needles may be composed of any conventional needle material, typically being a stainless steel, but could also be hard plastic.

Preferably, the access member 20 is preconnected or permanently affixed to the single common tube 60. Optionally, a connector 26, such as a luer connector may be provided to provide for removable connection. Even when the connector 26 is provided, however, it will be preferred that the connection be made prior to packaging of the system for storage and eventual use.

Alternatively, the percutaneous access member 20 may comprise a rigid access tube that is disposed at a generally right angle relative to the distal end of the single common tube 60. Such a configuration permits the access member to be percutaneously introduced into an implanted port 100 while the single common tube 60 remains generally parallel to or flat against the patient's skin. Such a "low profile" orientation of the catheter is advantageous since it reduces the risk of dislodgement, is more comfortable to the patient, and is generally easier to accommodate in a crowded medical therapy location. Such low profile access members and further details on suitable percutaneous access members can be found in commonly assigned, U.S. Pat. No. 5,997,524, the full disclosure of which is incorporated herein by reference.

Containers 30 and 50 may be made from a flexible polymer material which can contain used or unused dialysate. Containers 30 and 50 may be made from a variety of flexible or rigid materials so long as they provide a sterile containment and storage condition when they contain unused dialysate. In preferred embodiments of the present invention, the peritoneal dialysis tubing set 10 will typically have at least one container filled with unused dialysate, while the other container typically is empty to receive used dialysate from the patient. It is particularly critical that the container holding unused dialysate be maintained in a sterile condition in order to reduce the risk of infection to the peritoneal cavity. Sterility in the empty container which receives used dialysate is usually less critical as access to that container will be closed once the used dialysate has been drained from the patient's peritoneal cavity (discussed below). Though preferably also in a sterile condition, due to the less stringent requirements for sterility in the empty container, a greater variety of containers may be used as the empty container which receives the used dialysate.

Junction 40 comprises a three-way connector which allows the percutaneous access member 20 to be in fluid contact with either the first container 30, second container 50, or both containers simultaneously. As shown in FIG. 1, end 33 of tube 31 and end 53 of tube 51 are both connected to junction 40. In a preferred embodiment of junction 40, the junction comprises a Y-shaped connector having a first end 41 connected to end 33 of tube 31 and end 42 connected to end 53 of second tube 51. The junction 40 could comprise any other conventional three-way connector, such as a T-connector, or the like. A third end 43 of the junction 40 is fluidly coupled to single common tube 60 which leads to the percutaneous access member 20. It should be understood that a Y-shaped connector 40 could be replaced by equivalent known art devices such as particular types of directional flow valves which can selectively provide fluid access between container 30, second container 50, and percutaneous access member 20.

To access implantable mechanical port 100 as shown in FIG. 1, percutaneous access member 20 pierces the patient's skin S and penetrates through subcutaneous tissue T. Optionally, the member 20 passes through a tissue tract which has been previously formed and into an aperture on the implantable port 100. Suitable methods for access the port 100 with minimal trauma are described in U.S. Pat. No. 5,989,239 the full disclosure of which was previously incorporated.

FIG. 1 depicts a specific embodiment of the implantable mechanical port 100 having a representative peritoneal catheter 110 attached to the port. The implantable port 100 according to the present invention is implanted subcutaneously a short distance beneath the surface of the patient's skin S, typically being within about 3 mm to 20 mm of the skin's surface. For purposes of peritoneal dialysis, the implantable port 100 may be located in a variety of positions within the patient's body, such as over the rib cage of the patient, in the abdominal region of the patient, or in some other location deemed appropriate by the surgeon or doctor implanting the port 100. Implantable port 100 may be subcutaneously attached to the patient using adhesives, staples, sutures, or other attachment techniques known in the art. Suitable attachment techniques and further details of an implantable mechanical valve port are described in co-pending application Ser. No. 60/036,124, filed on Jan. 21, 1997; U.S. Pat. Nos. 5,931,801 and 5,931,829, each of which is assigned to the assignee of the present application. The full disclosures of each of these patents are incorporated herein by reference.

The peritoneal dialysis catheter 110 as shown in FIG. 1, passes through the peritoneum P and into the peritoneal cavity C. A specific embodiment of a peritoneal dialysis catheter, as shown in the figure, may assume a spiral configuration and have a plurality of outlet holes 111 along the length of the spiral-shaped catheter to facilitate diffusion of the dialysate into the peritoneal cavity C. Suitable peritoneal dialysis catheters are well known in the art.

The risk of infection in the peritoneal cavity is of particular concern to those patients using peritoneal dialysis to remove toxic by-products from their body. To mitigate against infecting the peritoneum or the peritoneal cavity during dialysate transfer, all connections between first container 30, second container 50, first tube 31, second tube 51, junction 40, single common tube 60, and percutaneous access member 20 may be permanently made or pre-connected to create a closed system within the peritoneal dialysis tubing set 10 prior to use. By using sealed connections between all major elements of the tubing set 10, the entry point of infectious material is limited to access provided by the percutaneous access member 20.

Figure 2:
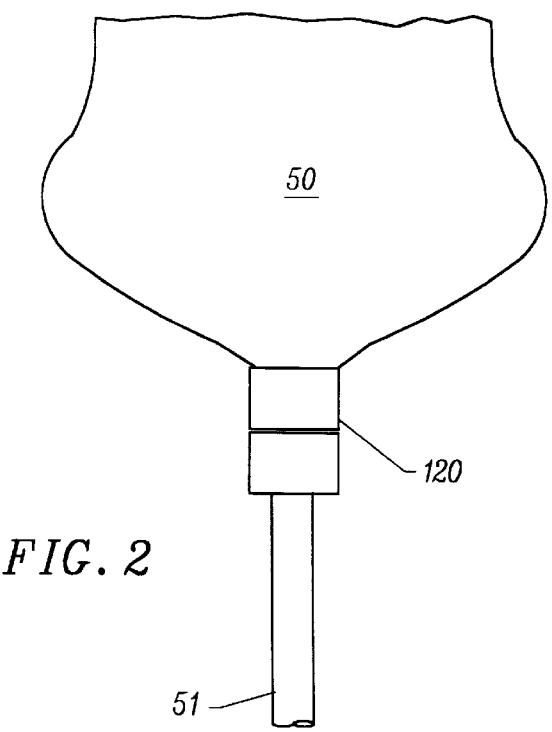
FIG. 2 illustrates a connector coupling a container and tube of the present invention.

In some instances, however, it may be desirable and advantageous to have releasable fluid couplings between particular elements of the tubing set 10. For example, assuming that second container 50 is the empty container receiving used dialysate from the peritoneal cavity, it may be desirable and advantageous to have a releasable fluid coupling 120 joining second tube 51 to the second container 50. Having a releasable coupling 120, as shown in FIG. 2, may allow the patient to use a greater variety of containers to contain the used dialysate as it is being drained from the peritoneal cavity C. This may provide for certain cost and manufacturing efficiencies.

Figure 3:
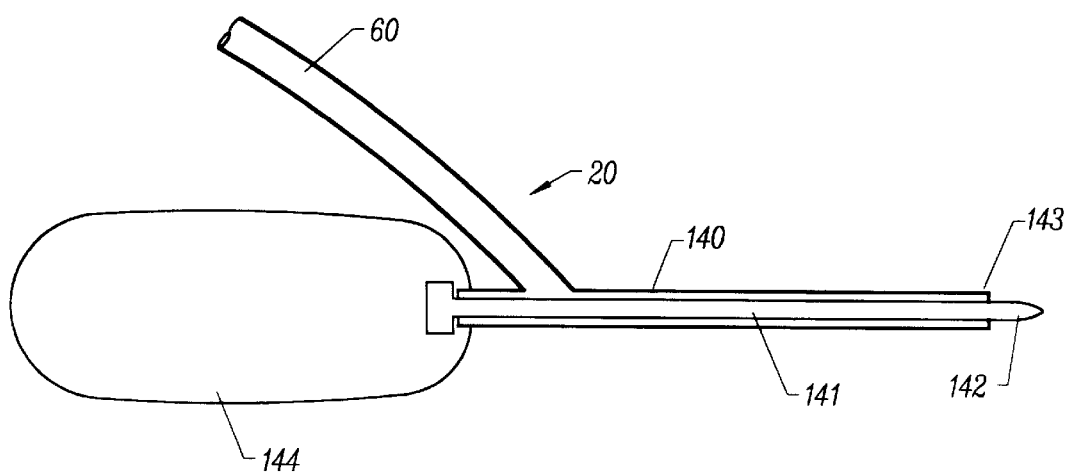
FIG. 3 shows an alternative embodiment of a percutaneous access member of the present invention.

In a further aspect of the invention, as shown in FIG. 3, the percutaneous access member 20 may comprise a tubular shaft 140 having a stylet 141 slidably disposed within the tubular shaft. A distal piercing end 142 on the stylet protrudes from distal end 143 of the shaft member 140 to provide percutaneous access to the implantable port 100. Once access has been achieved in the shaft member 140 is capable of accessing the implantable port 100, the stylet 141 can be proximally withdrawn within container 144 so that the stylet 141 does not interfere with fluid flow from single common tube 60. Container 144 ensures that the peritoneal dialysis tubing set 10 remains a closed system, even when stylet 141 has been proximally retracted.

Referring now to FIG. 4, an exemplary embodiment of the implantable port 100 will now be described in further detail. An exemplary port 100 comprising a base 212 and flexible conduit 214 is illustrated in FIGS. 4–7. As shown in FIG. 4, the flexible conduit 214 extends from the base 212 and terminates at a distal end fitting 216. Suitable conduit structures are described in U.S. Pat. No. 5,562,617, the full disclosure of which is incorporated herein by reference.

The fitting 216 will typically be a female fitting adapted to mate with a male fitting 218 at the proximal end of a dialysis catheter 110. Of course, it should be recognized that the fitting 218 could be attached to a catheter of some other design. Provision of a connector in the cannula intermediate the port and the lumenal connection has a number of benefits. The ability to implant the port 100 separately from the anchored end of the cannula, and then connect, simplifies implantation. For example, it is possible to make two relatively small incisions for implanting the port 100 and attaching the cannula, respectively, and then to tunnel subcutaneously to permit interconnection. Such an approach reduces patient trauma. Replacement of the port 100 and/or the cannula attachment is simplified since the two can be disconnected and one left undisturbed while the other is replaced. Such intermediate connections are preferably spaced relatively close to either the port or the lumenal connection, typically within 10 cm and often within 5 cm.

Figures 5A, 5B:
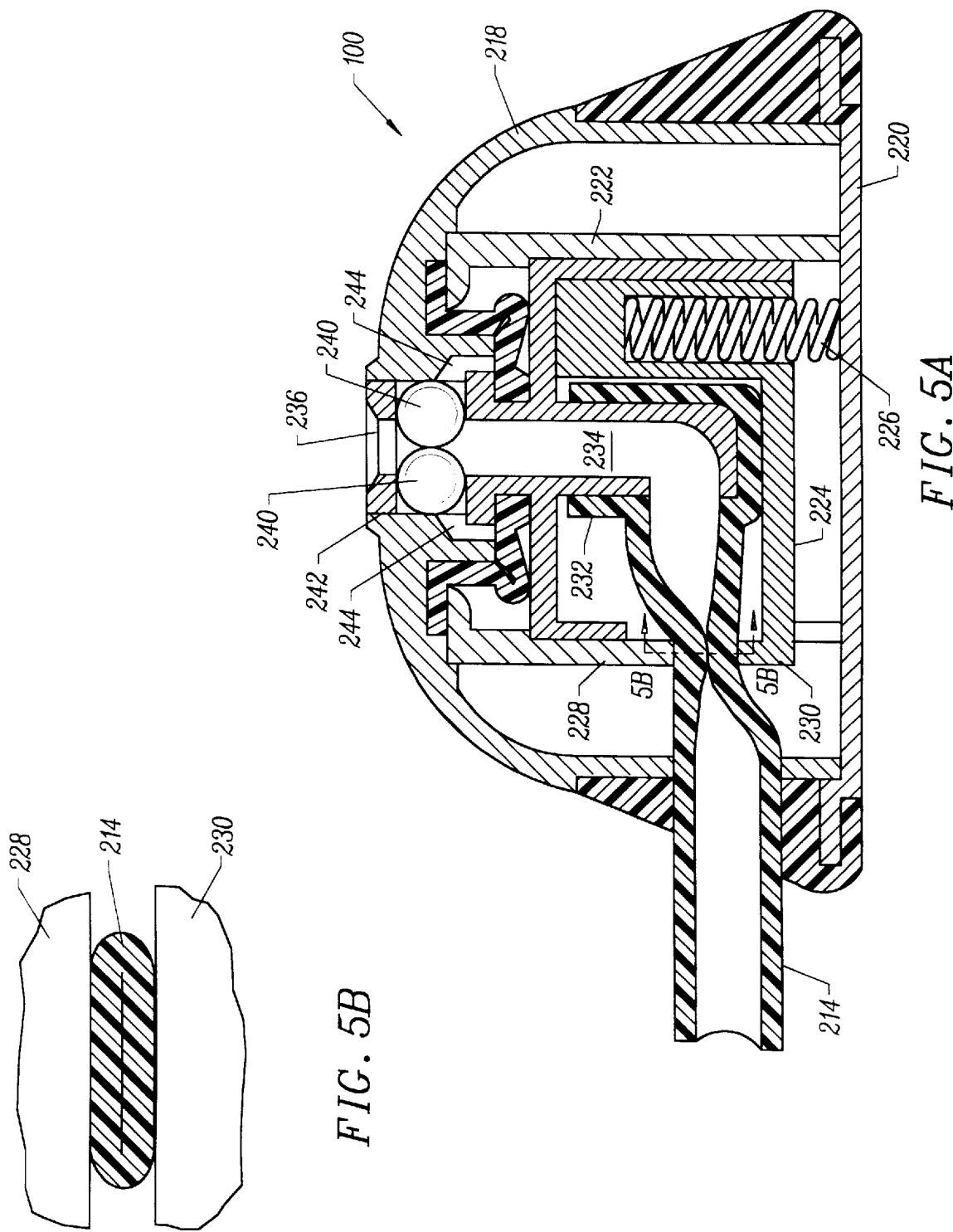
FIG. 5A is a side, cross-sectional view of the port of FIG. 4 shown with a closed internal valve structure.
FIG. 5B is a partial cross-sectional view taken along line 5B—5B of FIG. 5A.

Referring to FIG. 5A, the base 212 of implantable port 100 comprises an upper shell 218, a base plate 220, an internal cylinder 222, and a vertically reciprocating actuator block 224 disposed within the cylinder 222. A spring 226 urges the actuator block 224 upwardly relative to the cylinder 222. When the actuator block 224 is in its upward position, the conduit 214 is pinched closed between an upper lip 228 which is a portion of the wall of cylinder 222 and a lower lip 230 which is portion of the actuator block 224 (see FIG. 5B). Proximal end of the conduit 214 is connected to the lower end of a tube 232 which depends into an interior volume of the actuator block 224. The depending tube 232 provides an axial bore 234 for receiving a percutaneous access member 20.

Referring to FIG. 5C, the access member 20 is introduced through an opening 236 at the upper end of the axial bore 234. Typically, though not necessarily, the opening 236 has a slight conical shape to facilitate alignment of the access member 20 as it is introduced into the bore 234. A pair of balls 240 are disposed in an upper portion of the tube 232 and contained within a circular aperture 242 in the shell 218 on the actuator block 224 as in its raised configuration, as shown in FIG. 5A. When access member 20 is introduced through the opening 236, it will encounter the balls 240 and depress the actuator block 224 downward until the block reaches its lower configuration. At that time, the balls 240 will move radially outward into an expanded portion 244 of the aperture 242. The balls 240 will thus become locked within the expanded region 244 so long as the access member 20 remains in place.

When the actuator block 224 has been lowered, as shown FIGS. 5C and 5D, the opposed lips 228 and 230 are opened in order to relieve external clamping on the conduit 214. Thus, as the access member 20 is inserted into the implantable port 210, the clamping mechanism which has previously closed the flexible conduit 214 will be opened. When the access member 20 is removed, the spring 226 will urge the actuator block 224 upwardly, and the implantable port will return to the configuration shown in FIGS. 5A and 5B.

Referring now to FIGS. 6 and 7, another alternative flexible conduit 314 which may be attached to base 212 of an implantable port 100 is illustrated. The flexible conduit 314 is formed integrally with the silicone overmolding 350, thus firmly anchoring the conduit to the base 212. While the internal portions of the conduit 314 are identical to those of conduit 214 and the earlier embodiments, the external portion of the conduit includes rib structures 318 in order to enhance hoop strength of the conduit. Moreover, a distal connector 316 is provided for connection to a male connector 320 at the proximal end of a catheter. The connector 320 comprises a metal, usually titanium, fitting which is received within the lumen of the silicone conduit 314. A clip 330 is provided for securing over the connectors 316 and 320 after the port 312 and catheter have both been implanted and connected. The catheter connection mechanism shown in FIG. 6 is particularly advantageous since the catheter may be disconnected from the flexible conduit 314 without having to disturb the implantation of the base 212 of the port 100.

A method for performing peritoneal dialysis using the peritoneal dialysis tubing set 10 of FIG. 1, will be described with reference to FIGS. 1 and 8–10. The configuration of the peritoneal dialysis tubing set 10 as shown in FIG. 1, is used for filling the peritoneal cavity with unused dialysate when the cavity is empty. As there is no used dialysate to drain from the cavity, the configuration as shown does not position the empty second container 50 to receive dialysate from the patient.

Figure 8:
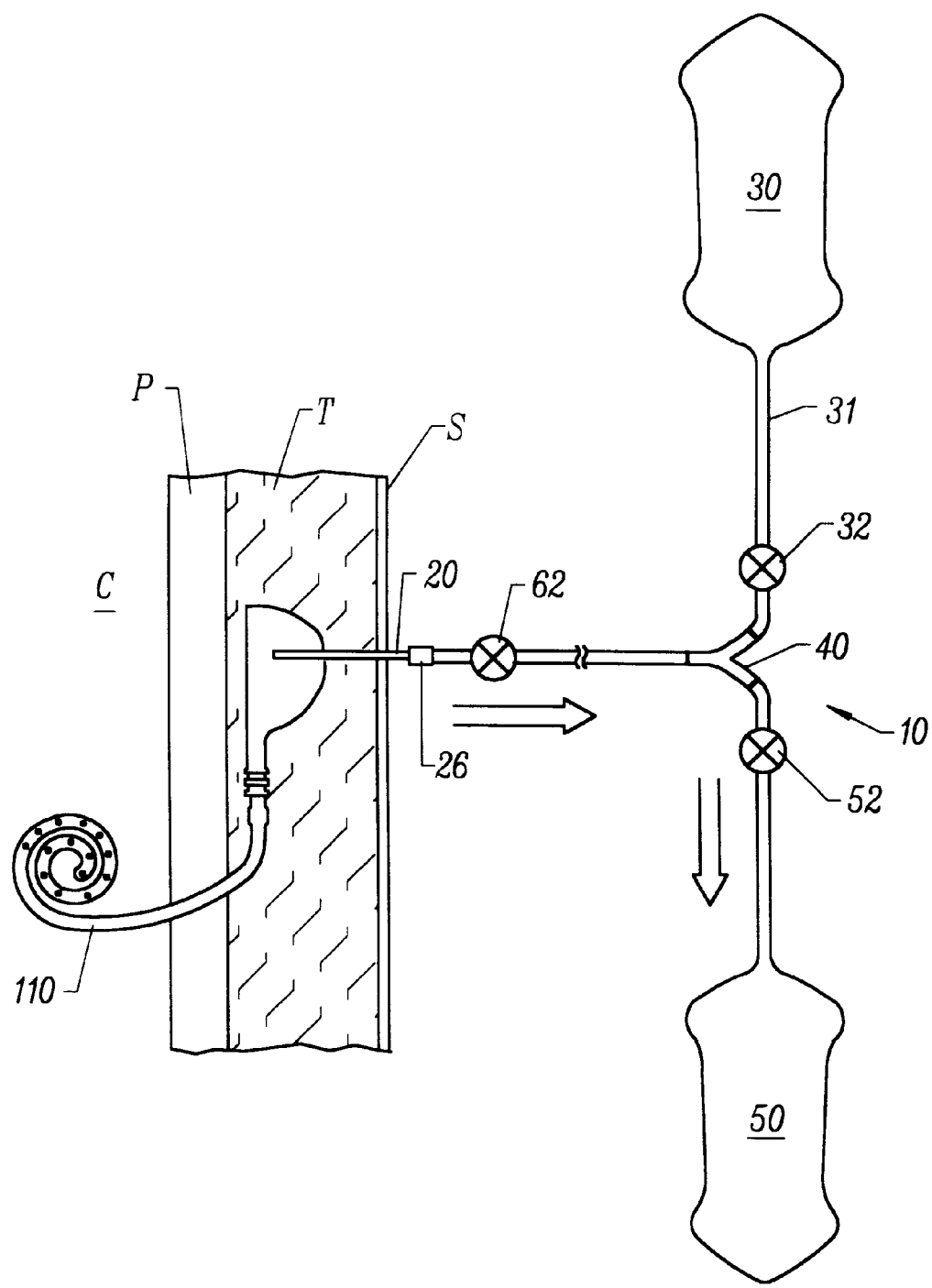
FIG. 8 is a schematic illustration of the system of FIG. 1 with the containers positioned to deliver and drain fluid to and from the patient.

Referring now to FIG. 8, the configuration of the peritoneal dialysis tubing set 10 is more typical of what will be found when used dialysate must be drained from the peritoneal cavity and unused dialysate must be delivered to refill the cavity. Initially, percutaneous access member 20 is inserted through the skin of the patient and into an aperture in the implantable port 100 for receiving the percutaneous access member. Once the percutaneous access member 20 has been properly positioned, the member 20 will be fluidly coupled with the peritoneal dialysis catheter 110. At this stage, fluid flow controller 62 and 52 will be in an open condition so as to provide a fluid pathway between the peritoneal cavity and empty, second container 50. Fluid flow controller 32 will be in a closed condition to prevent fluid contact between unused dialysate and the used dialysate flowing from the peritoneal cavity C. Typically, drainage of the used dialysate occurs solely under the force of gravity. Alternatively, it may be possible to use a pump to increase the flow rate from the peritoneal cavity (not shown).

Figure 9:
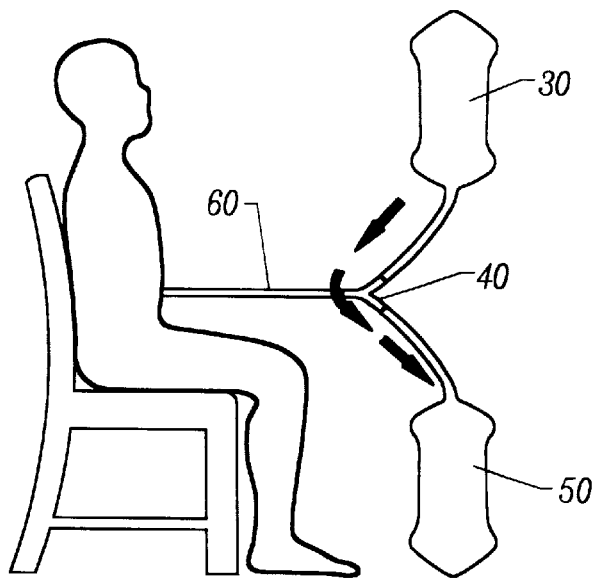
FIGS. 9–10 show a flushing step and a filling step using the system of FIG. 1.
Figure 10:
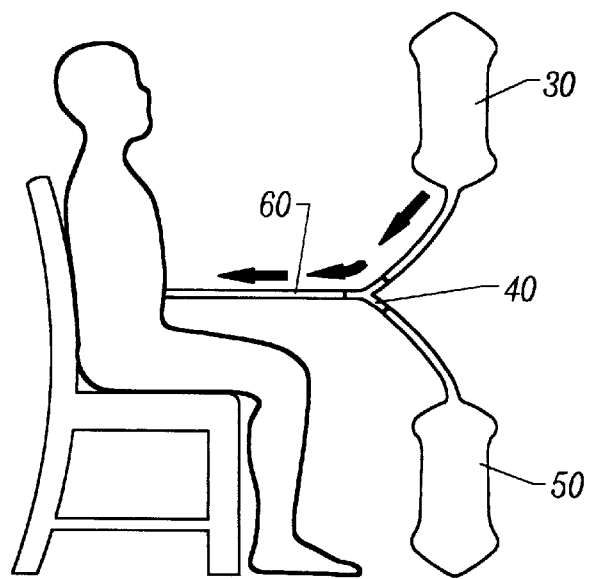

Once drainage of the dialysate into second container 50 has been completed, fluid flow controller 62 will be placed in a closed condition. Referring now to FIG. 9, fluid flow controller 32 will now be opened to flush portions of tube 31 and single common tube 60. Flow controller 52 will remain open during this flushing procedure, so as to allow the dialysate being flushed to flow into second container 50. It is generally understood in the art that one of the advantages of using a Y-set tubing set is that it allows for this type of flushing to remove contaminants in the flow pathway prior to filling the peritoneal cavity with unused dialysate. The flushing typically occurs for about 5 to 10 seconds.

Once the flushing has been completed, flow controller 52 will be closed, restricting access to second container 50. Flow controller 62 will now be opened to as to allow unused dialysate solution to flow from first container 30 through the tubing set 10, and eventually into peritoneal dialysis catheter 110. The flow occurs as shown by the arrows in FIG. 10. Again, the filling process typically occurs solely under the force of gravity, although pumps or other devices may be used to assist the filling process. Once the transfer or delivery of unused dialysate into the peritoneal cavity of the patient has been completed, fluid flow controller 62 and 32 will be closed and percutaneous access member 20 will be retracted from the patient. A bandage or some other coverage device may be used to protect the percutaneous access site on the patient during the 4 to 6 hour dwell period of the dialysate within the peritoneal cavity. With the transfer of dialysate completed, the patient is free to perform daily activities without the restriction of having to carry a used dialysate container or a filtration device associated with hemodialysis.

Although the foregoing invention has been described in some detail by way of illustration and example, for purposes of clarity of understanding, it will be obvious that certain changes and modifications may be practiced within the scope of the appended claims.

What is claimed is:

1. An apparatus for use in a patient for peritoneal dialysis, the apparatus comprising:
    a first container at least partially filled with dialysate;
    a second, substantially empty container;
    a first flexible tube fluidly coupled to the first container;
    a second flexible tube which may be fluidly coupled to the second, substantially empty container;
    a three-way junction fluidly coupled to the ends of the first and second tubings;
    a single common tube fluidly coupled to said junction and being fluidly connected to said first and second tubes through said junction; and
    a percutaneous access member having a sharpened end to puncture tissue connected to the end of the single common tube for flowing dialysate to and from the patient, said member having a bore diameter of at least 1.16 mm and adapted to removably engage an opening of an implanted device within said patient, said access member configured to engage said opening to define a fluid pathway directing substantially all fluid flow into said implanted device.

2. The apparatus of claim 1, wherein the percutaneous access member is straight, has a length in the range from 15 mm to 40 mm, and a bore diameter in the range from 1.16 mm to 5 mm.

3. The apparatus of claim 2, wherein the percutaneous access member is a fistula needle.

4. The apparatus of claim 2, wherein the percutaneous access member has a blunt distal tip.

5. The apparatus of claim 2, wherein the percutaneous access member comprises a tubular shaft having a stylet removably housed within the shaft.

6. The apparatus of claim 1, wherein the percutaneous access member is disposed at a generally right angle relative to a distal end of the single common tube.

7. The apparatus of claim 1, wherein the percutaneous access member has a connector removably connecting the member to the single common tube.

8. The apparatus of claim 1, wherein the first and second tubes each have a access member connector for removably coupling the tube to the container.

9. The apparatus of claim 1, wherein the first, second, and single common tubes each have a fluid flow controller on said tubes.

10. The apparatus of claim 1, wherein the three way connector has a Y-shape.

11. The apparatus of claim 10, wherein the first container is permanently connected to said first flexible tube, the second container is permanently connected to said second flexible tube, and the common tube is permanently connected to the access member.

12. The apparatus of claim 11, further comprising at least one fluid flow controller on said first flexible tube.

13. The apparatus of claim 10, wherein the access member is adapted to introduce dialysate at flow rates between about 100 to 200 ml/min.

14. The apparatus of claim 1, wherein the percutaneous access member is straight, has a length in the range from 15 mm to 40 mm, and a bore diameter in the range from 1.16 mm to 5 mm.

15. The apparatus of claim 14, wherein the percutaneous access member is a fistula needle.

16. The apparatus of claim 14, wherein the percutaneous access member has a blunt distal tip.

17. The apparatus of claim wherein the percutaneous access member comprises a tubular shaft having a stylet removably housed within the shaft.

18. A system for performing peritoneal dialysis comprising:
   a) a peritoneal dialysis tubing set having an access member having a bore diameter of at least 1.16 mm and fluidly coupled by a flexible tube to a container at least partially filled with dialysate, said tube having a three-way junction; and
   b) a mechanical port having
      a base with an aperture for receiving the access member of the tubing set,
      a flexible conduit in the port disposed to establish fluid flow with the access member inserted through the first passage, and
      a linkage assembly in the port which opens the flexible conduit when the access member is present in the passage and collapses the flexible conduit when the access member is absent from the passage.

19. A system of claim 18, wherein said linkage assembly comprises:
   an actuator assembly reciprocatably received in the base having a bore aligned with the first passage for receiving the needle, wherein a proximal end of the flexible conduit is mechanically coupled to the bore in the actuator assembly; and
   a spring for urging the actuator assembly to a first position in the base wherein the relative position of the actuator assembly and the second passage closes the flexible conduit and wherein insertion of the access tube into the first passage shifts the actuator assembly to a second position which opens the flexible conduit.

20. A system of claim 18, further comprising a peritoneal dialysis catheter fluidly coupled to said flexible conduit of the mechanical port.

21. A system of claim 18 further comprising:
   a second flexible tube coupled to said three-way junction;
   a second, substantially empty container coupled to said second flexible tube.

22. A system of claim 21 further comprising a separate connector for coupling said second container to the second flexible tube.

23. A system of claim 18 further comprising at least one fluid flow controller on the flexible tube.

24. A system of claims 18 wherein the three-way junction has a Y-shape.

25. A system of claim 21 wherein the second container has a position lower than the percutaneous access member to facilitate gravity assisted flow of dialysate from the patient.

26. A system of claim 18 wherein the access member is adapted to deliver dialysate at flow rates between about 100 to 200 ml/min.

27. An apparatus for use in a patient for peritoneal dialysis, the apparatus comprising:
   a first container at least partially filled with dialysate;
   a second, substantially empty container;
   a first flexible tube fluidly coupled to the first container;
   a second flexible tube which may be fluidly coupled to the second, substantially empty container;
   a three-way junction fluidly coupled to the ends of the first and second tubings;
   a single common tube fluidly coupled to said junction and being fluidly connected to said first and second tubes through said junction; and
   a rigid percutaneous access member connected to the end of the single common tube for flowing dialysate to and from the patient, said member having a bore diameter of at least 1.16 mm and a sharpened end to puncture tissue and to removably engage an opening of an implanted device within said patient.

28. The apparatus of claim 27, wherein the percutaneous access member is disposed at a generally right angle relative to a distal end of the single common tube.

29. The apparatus of claim 27, wherein the percutaneous access member has a connector removably connecting the member to the single common tube.

30. The apparatus of claim 27, wherein the first and second tubes each have a access member connector for removably coupling the tube to the container.

31. The apparatus of claim 27, wherein the first, second, and single common tubes each have a fluid flow controller on said tubes.

32. The apparatus of claim 27, wherein the three way connector has a Y-shape.

33. The apparatus of claim 32, wherein the first container is permanently connected to said first flexible tube, the second container is permanently connected to said second flexible tube, and the common tube is permanently connected to the access member.

34. The apparatus of claim 33, further comprising at least one fluid flow controller on said first flexible tube.

35. The apparatus of claim 32, wherein the access member is adapted to introduce dialysate at flow rates between about 100 to 200 ml/min.

36. An apparatus for use in a patient for peritoneal dialysis, the apparatus comprising:

a first container at least partially filled with dialysate;

a second, substantially empty container;

a first flexible tube fluidly coupled to the first container;

a second flexible tube which may be fluidly coupled to the second, substantially empty container;

a three-way junction fluidly coupled to the ends of the first and second tubings;

a single common tube fluidly coupled to said junction and being fluidly connected to said first and second tubes through said junction; and a fistula needle connected to the end of the single common tube for flowing dialysate to and from the patient, said member having a bore diameter of at least 1.16 mm and adapted to removably engage an opening of an implanted device within said patient.

\* \* \* \* \*